United States Patent
Elomari et al.

(10) Patent No.: US 8,304,574 B2
(45) Date of Patent: *Nov. 6, 2012

(54) BIOLUBRICANT ESTERS FROM THE ALCOHOLS OF UNSATURATED FATTY ACIDS

(75) Inventors: Saleh A. Elomari, Fairfield, CA (US); Stephen Joseph Miller, San Francisco, CA (US); Zhen Zhou, Emeryville, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/344,477

(22) Filed: Jan. 5, 2012

(65) Prior Publication Data

US 2012/0108834 A1    May 3, 2012

Related U.S. Application Data

(62) Division of application No. 12/480,032, filed on Jun. 8, 2009, now Pat. No. 8,188,019.

(51) Int. Cl.
C07C 249/00 (2006.01)
C07C 67/02 (2006.01)

(52) U.S. Cl. .................. 560/353; 560/263
(58) Field of Classification Search .......... 560/353, 560/263

See application file for complete search history.

(56) References Cited

U.S. PATENT DOCUMENTS 4,474,940 A * 10/1984 Wilk et al. ............... 528/295.3

* cited by examiner

*Primary Examiner* — Jafar Parsa
(74) *Attorney, Agent, or Firm* — Penny Prater; Jeffrey M. McQuiston

(57) ABSTRACT

The present invention is generally directed to triester-based lubricant compositions. The present invention is also directed to methods of making these and other similar lubricant compositions. In some embodiments, the methods for making such triester-based lubricants utilize a biomass precursor comprising mono-unsaturated fatty acids, wherein such mono-unsaturated fatty acids are reduced to mono-unsaturated fatty alcohols en route to the synthesis of triester species for use as/in the triester-based lubricant compositions. Subsequent steps in such synthesis may employ carboxylic acids and/or acyl halides/anhydrides derived from biomass and/or Fischer-Tropsch synthesis.

8 Claims, 4 Drawing Sheets

Table 1. Physical properties of triester compound 1

| Viscosity @ 100°C | 5.2 mm$^2$/s (cSt) |
|---|---|
| Viscosity Index | 140 |
| Cloud Point | -23°C |
| Pour Point | -31°C |
| Oxidation Stability | 28.8 hrs/L O$_2$ uptake |

*Fig. 4*

BIOLUBRICANT ESTERS FROM THE ALCOHOLS OF UNSATURATED FATTY ACIDS

PRIORITY TO RELATED APPLICATIONS

This application is a divisional application of application of U.S. Ser. No. 12/480,032, filed Jun. 8, 2009 now U.S. Pat. No. 8,188,019 and claims priority thereto.

FIELD OF THE INVENTION

This invention relates to ester-based lubricants and specifically to triester-based lubricants and their manufacture—particularly wherein they are made from at least one biologically-derived precursor.

BACKGROUND

Esters have been used as lubricating oils for over 50 years. They are used in a variety of applications ranging from jet engines to refrigeration. In fact, esters were the first synthetic crankcase motor oils in automotive applications. However, esters gave way to polyalphaolefins (PAOs) due to the lower cost of PAOs and their formulation similarities to mineral oils. In full synthetic motor oils, however, esters are almost always used in combination with PAOs to balance the effect on seals, additives solubility, volatility reduction, and energy efficiency improvement by enhanced lubricity.

Ester-based lubricants, in general, have excellent lubrication properties due to the polarity of the ester molecules of which they are comprised. The polar ester groups of such molecules adhere to positively-charged metal surfaces creating protective films which slow down the wear and tear of the metal surfaces. Such lubricants are less volatile than the traditional lubricants and tend to have much higher flash points and much lower vapor pressures. Ester-based lubricants are excellent solvents and dispersants, and can readily solvate and disperse the degradation by-products of oils. Therefore, they greatly reduce sludge buildup. While ester-based lubricants are stable to thermal and oxidative processes, the ester functionalities give microbes a handle to do their biodegrading more efficiently and more effectively than their mineral oil-based analogues. However, the preparation of esters is more involved and more costly than the preparation of their PAO counterparts.

Triester-based lubricants and their manufacture have been recently reported, wherein the triester species have a general formula:

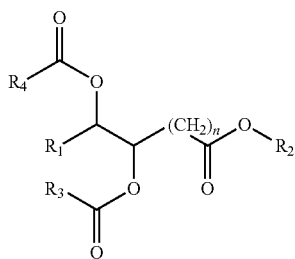

where $R_{1-4}$ are the same or independently selected from $C_2$ to $C_{20}$ hydrocarbon groups, and n is an integer from 2 to 20. See commonly-assigned U.S. patent application Ser. No. 12/122,894; filed Apr. 4, 2007 and published as United States Patent Publication No. 20080248982. Note that the ester group comprising $R_2$ is attached to the aliphatic backbone via an inverted (non-homologous) linkage (compared to the ester groups comprising $R_3$ and $R_4$).

In view of the foregoing, and not withstanding such above-described advances in triester-based lubricant synthesis, facile methods of generating triester-based lubricants would be extremely useful—particularly wherein the triester species in said lubricants comprise homologous linkages between all three ester groups and the aliphatic backbone.

BRIEF DESCRIPTION OF THE INVENTION

The present invention is generally directed to triester-based lubricant compositions. The present invention is also directed to methods of making these and other similar lubricant compositions. In some embodiments, the methods for making such triester-based lubricants at least partially make use of one or more biomass precursors. In these or other embodiments, lubricant precursor species can also be sourced or derived from Fischer-Tropsch (FT) reaction products/byproducts.

In some embodiments, the present invention is directed to a lubricant composition comprising a quantity of at least one triester species, the triester species having the following structure:

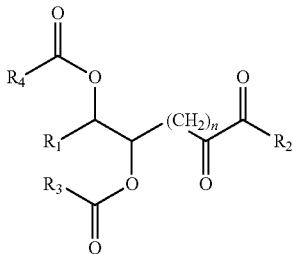

wherein $R_1$, $R_2$, $R_3$, and $R_4$ are the same or independently selected from $C_2$ to $C_{20}$ hydrocarbon groups, and wherein "n" is a number from 2 to 20.

In some embodiments, the kinematic viscosity of the above-described composition at a temperature of 100° C. is at least 3 mm²/s, i.e., centistokes (cSt). In some or other embodiments, said composition has a pour point of less than −20° C.

For the above-described composition, $R_1$ is typically selected to have a total carbon number of from at least about 6 to at most about 12, $R_3$ and $R_4$ are typically selected to have a combined carbon number from at least about 2 to at most about 40, $R_2$ is typically selected to have a carbon number from at least about 1 to at most about 20, and "n," as denoted in —$(CH_2)_n$— in the above structure, is typically an integer in the range of from at least about 5 to at most about 10. Typically, for the lubricant composition described above, the at least one triester species has a molecular mass that is from at least about 400 atomic mass units (a.m.u.) to at most about 1100 a.m.u. More typically, the at least one triester species has a molecular mass that is from at least about 450 a.m.u. to at most about 1000 a.m.u.

In some embodiments, at least one triester species in the above-described lubricant composition is selected from the group consisting of octadecane-1,9,10-triyl trihexanoate (1); octadecane-1,9,10-triyl triheptanoate; octadecane-1,9,10-triyl trioctanoate (2); octadecane-1,9,10-triyl trinonoate; octadecane-1,9,10-triyl tris(decanoate) (3); octadecane-1,9,10-triyl tridodecanoate (4); octadecane-1,9,10-triyl triundecanoate; octadecane-1,9,10-triyl tridodecanoate; octadecane- 1,9,10-triyl tridecanoate; and octadecane-1,9,10-triyl tritetradecanoate (5); and mixtures thereof. For corresponding structures of compounds 1-5, see FIG. 1 (vide infra).

In some embodiments, the above-described composition comprises quantities of at least two different triester species. In some or other embodiments, said composition further comprises a base oil selected from the group consisting of Group I oils, Group II oils, Group III oils, and combinations thereof. Additionally or alternatively, in some embodiments, said composition further comprises one or more diester species.

In some embodiments, the present invention is directed to methods of making the above-described composition(s), such methods comprising the steps of: (a) reducing a mono-unsaturated fatty acid having a carbon number of from 10 to 22 with a metal hydride so as to form an unsaturated fatty alcohol; (b) epoxidizing the unsaturated fatty alcohol to form an epoxy-alcohol species comprising an epoxide ring; (c) opening the ring of the epoxy-alcohol species to form a triol; and (d) esterifying the triol with an esterifying species to form a triester species, wherein the esterifying species is selected from the group consisting of carboxylic acids, acyl halides, acyl anhydrides, and combinations thereof, and wherein the esterifying species have a carbon number of from 2 to 18. In some such embodiments, said method can yield a mixture of triester species within the resulting lubricant composition by utilizing, in one or both of steps (a) and (d), reagents (e.g., mono-unsaturated fatty acids and esterifying species) that comprise a range of carbon number.

In some embodiments, such above-described methods further comprise a step of blending the triester species with other triester species. In some or other embodiments, such methods can further comprise a step of blending the triester species with one or more diester species. In some or still other embodiments, such methods can further comprise a step of blending the triester species with a base oil selected from the group consisting of Group I oils, Group II oils, Group III oils, and combinations thereof.

In some particular embodiments, wherein the above-described method uses oleic acid as a representative mono-unsaturated fatty acid, the resulting triester is of the type:

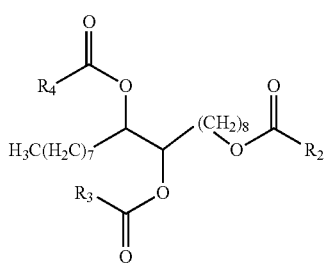

wherein $R_2$, $R_3$ and $R_4$ are typically the same or independently selected from $C_2$ to $C_{20}$ hydrocarbon groups, and are more typically selected from $C_4$ to $C_{12}$ hydrocarbon groups.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 4 (Table 1) tabularizes lubrication properties of triester species 1.

DETAILED DESCRIPTION OF THE INVENTION

1. Introduction

Figure 1:
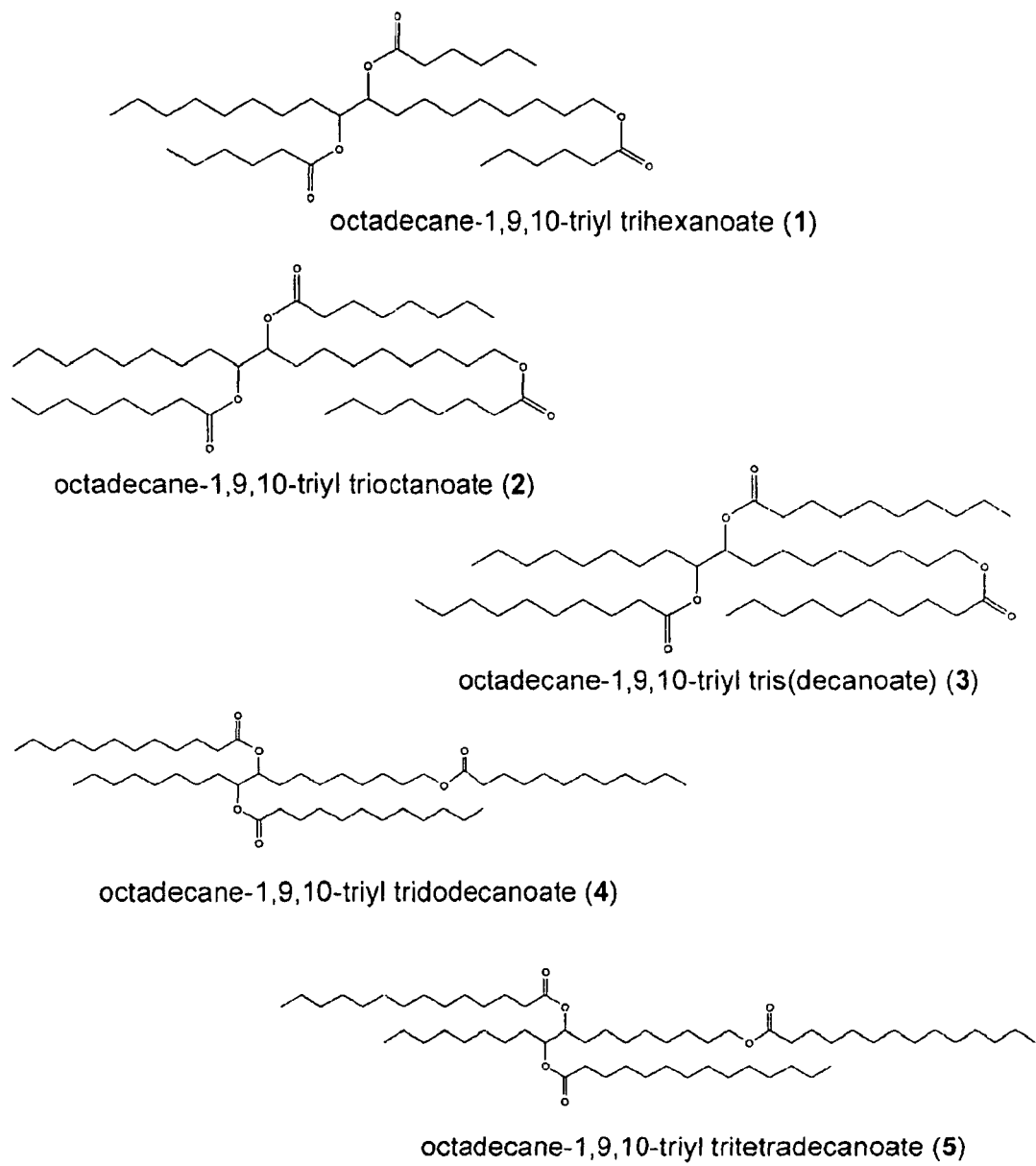
FIG. 1 depicts five exemplary triester-based compounds 1-5, suitable for use as lubricants and/or lubricant components, in accordance with some embodiments of the present invention.

The present invention is generally directed to triester-based lubricant compositions. The present invention is also directed to methods of making these and other similar lubricant compositions. In many of these embodiments, the methods for making such triester-based lubricants utilize a biomass precursor, wherein it is typically at least the fatty (carboxylic) acids utilized in such methods that are obtained from biomass sources (e.g., vegetable oil and/or algae). Other chemical components used in such methods can be derived from biomass or other sources such as, but not limited to, Fischer-Tropsch (FT) synthesis products and/or by-products.

Because biolubricants and biofuels are increasingly gaining ground and becoming topics of focus for many in the oil industry, the use of biomass in the making of such above-mentioned lubricants could be attractive from several different perspectives. To the extent that biomass is so utilized in making the triester-based lubricants of the present invention, such lubricants are deemed to be biolubricants.

An advantage of the tri-ester lubricants described herein in at least some embodiments is that they can be entirely bio-derived, i.e., all of the reagents used in their synthesis (exclusive of solvents and catalysts) can be derived from a biological precursor material. Additionally, methods for producing such lubricants make use of the olefins already present in vegetable/crop oils, thereby streamlining the synthetic process. Additionally still, as opposed to conventional triester biolubricants, i.e., triglycerides, the tri-ester lubricants described herein in at least some embodiments generally have excellent low temperature properties without having carbon-carbon double bonds (which would compromise oxidation stability).

2. Definitions

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See, e.g., ASTM Standard Test Method D 5950-02 (R 2007).

"Cloud point," as defined herein, represents the temperature at which a fluid begins to phase separate due to crystal formation. See, e.g., ASTM Standard Test Method D 5771-05.

"Centistoke," abbreviated "cSt," is a unit for kinematic viscosity of a fluid (e.g., a lubricant), wherein 1 centistoke equals 1 millimeter squared per second (1 cSt=1 mm²/s). See, e.g., ASTM Standard Guide and Test Method D 2270-04.

"Oxidation stability," as defined herein, generally refers to a composition's resistance to oxidation. Oxidator BN is a convenient way to measure the oxidation stability of base oils, and it is the method used to evaluate the oxidation stability of at least some of the lubricant compositions described herein. The Oxidator BN test is described by Stangeland et al. in U.S. Pat. No. 3,852,207. The Oxidator BN test measures an oil's resistance to oxidation by means of a Dornte-type oxygen absorption apparatus. See Dornte "Oxidation of White Oils," Industrial and Engineering Chemistry, vol. 28, pp. 26-30, 1936. Normally, the conditions are one atmosphere of pure oxygen at 340° F. (171° C.). The results are reported in hours to absorb 1000 mL (1 L) of $O_2$ by 100 grams of oil.

With respect to describing molecules and/or molecular fragments herein, "$R_m$," where "m" is merely an identifier, refers to a hydrocarbon group, wherein the molecules and/or molecular fragments can be linear and/or branched, and unless stated otherwise, groups identified by different "m" identifiers can be the same or different.

As defined herein, "carbon number," as it relates to a hydrocarbon molecule or fragment (e.g., an alkyl group), is an integer denoting the total number of carbon atoms in the fragment or molecule. Carbon number with such a fragment or molecule can also be denoted as "$C_n$," where "n" is the total number of carbon atoms within that particular fragment or molecule.

The prefix "bio," as used herein, refers to an association with a renewable resource of biological origin, such as resource generally being exclusive of fossil fuels.

"Fischer-Tropsch products," as defined herein, refer to molecular species derived from a catalytically-driven reaction between CO and $H_2$ (i.e., "syngas"). See, e.g., Dry, "The Fischer-Tropsch process: 1950-2000," vol. 71(3-4), pp. 227-241, 2002; Schulz, "Short history and present trends of Fischer-Tropsch synthesis," Applied Catalysis A, vol. 186, pp. 3-12, 1999.

3. Triester Lubricant Compositions

In some embodiments, the present invention is generally directed to triester-based lubricant compositions comprising a quantity of triester species having the following chemical structure:

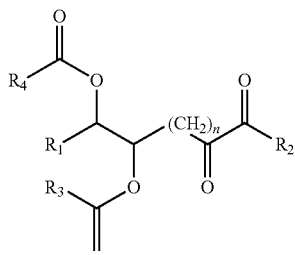

wherein $R_1$, $R_2$, $R_3$, and $R_4$ are the same or independently selected from $C_2$ to $C_{20}$ hydrocarbon groups (groups with a carbon number from 2 to 20), and wherein "n" is an integer from 2 to 20.

Regarding the above-mentioned triester species, selection of $R_1$, $R_2$, $R_3$, $R_4$, and n can follow any or all of several criteria. For example, in some embodiments, $R_1$, $R_2$, $R_3$, $R_4$ and n are selected such that the kinematic viscosity of the composition at a temperature of 100° C. is typically 3 mm²/s, i.e., centistokes (cSt) or greater. In some or other embodiments, $R_1$, $R_2$, $R_3$, $R_4$ and n are selected such that the pour point of the resulting lubricant is −20° C. or lower. In some embodiments, $R_1$ is selected to have a total carbon number of from 6 to 12. In these or other embodiments, $R_2$ is selected to have a carbon number of from 1 to 20. In these or other embodiments, $R_3$ and $R_4$ are selected to have a combined carbon number of from 4 to 36. In these or other embodiments, n is selected to be an integer from 5 to 10. Depending on the embodiment, such resulting triester species can typically have a molecular mass between 400 atomic mass units (a.m.u.) and 1100 a.m.u, and more typically between 450 a.m.u. and 1000 a.m.u.

In some embodiments, such above-described compositions are substantially homogeneous in terms of their triester component. In some or other embodiments, the triester component of such compositions comprises a variety (i.e., a mixture) of such triester species. In these or other embodiments, such above-described lubricant compositions further comprise one or more diester species.

Referring to FIG. 1, in some of the above-described embodiments, the triester-based lubricant composition comprises one or more of the exemplary triester species shown, i.e., one or more of the following: octadecane-1,9,10-triyl trihexanoate (1); octadecane-1,9,10-triyl triheptanoate; octadecane-1,9,10-triyl trioctanoate (2); octadecane-1,9,10-triyl trinonoate; octadecane-1,9,10-triyl tris(decanoate) (3); octadecane-1,9,10-triyl tridodecanoate (4); octadecane-1,9,10-triyl triundecanoate; octadecane-1,9,10-triyl tridodecanoate; octadecane-1,9,10-triyl tridecanoate; and octadecane-1,9,10-triyl tritetradecanoate (5). In some embodiments, the triester-based lubricant composition further comprises a base oil selected from the group consisting of Group I oils, Group II oils, Group III oils, and mixtures thereof.

It is worth noting that in many applications, the above-described triesters and their compositions are not used as lubricants by themselves, but are used as blending stocks. As such, esters with higher pour points may also be used as blending stocks with other lubricant oils since they are very soluble in hydrocarbons and hydrocarbon-based oils.

4. Methods of Making Triester Lubricants

As mentioned above, the present invention is additionally directed to methods of making the above-described lubricant compositions and/or the triester compositions contained therein.

Figure 2:
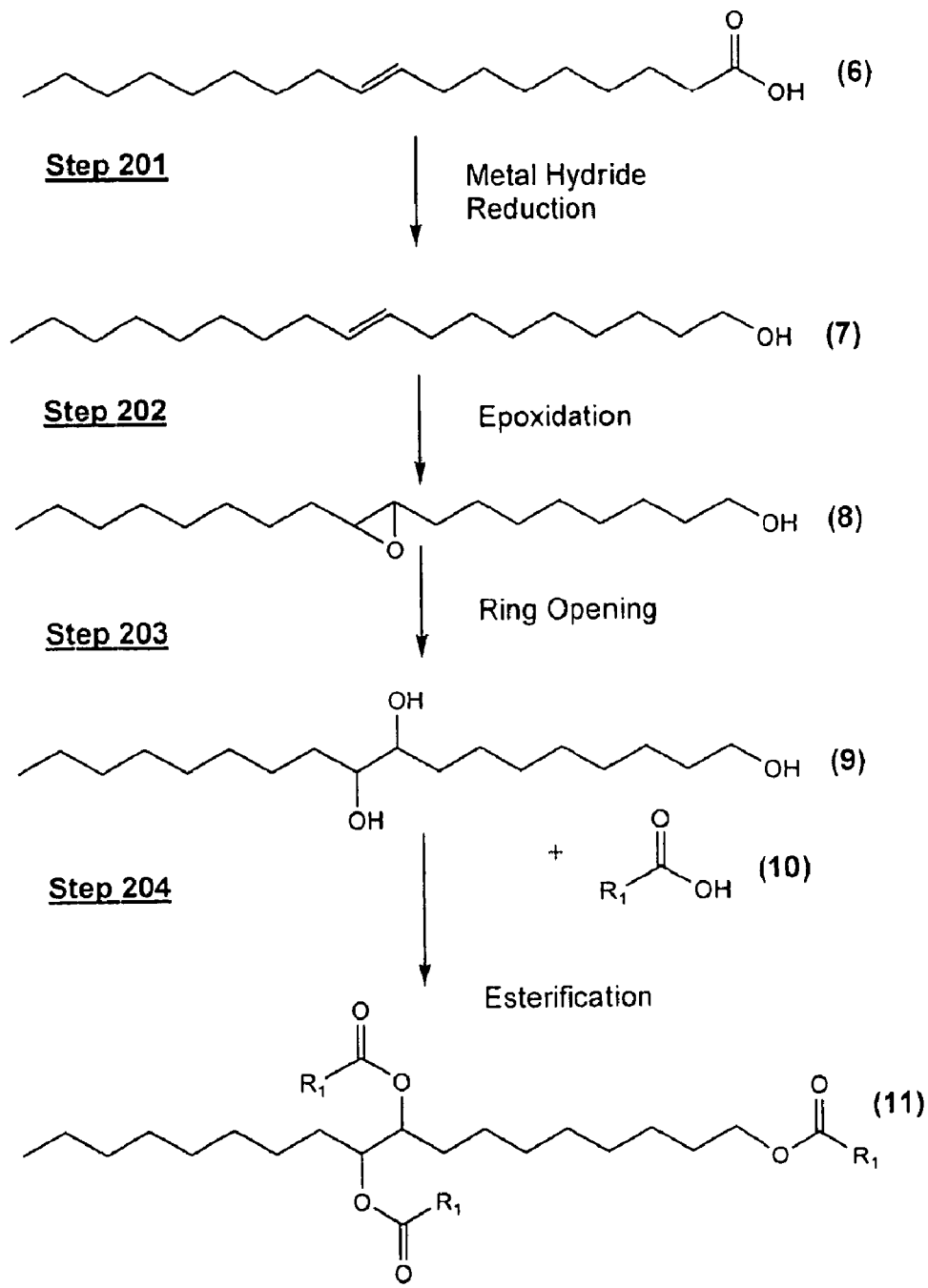
FIG. 2 (Scheme 1) is a chemical flow diagram generally illustrating methods of making a triester-based lubricant composition, in accordance with some embodiments of the present invention, wherein oleic acid is used as a representative mono-unsaturated fatty acid.

Referring to the chemical flow diagram shown in FIG. 2 (Scheme 1), in some embodiments, processes/methods for making the above-mentioned triester-based compositions, typically having lubricating base oil viscosity and pour point, comprise the following steps: (Step 201) reducing a mono-unsaturated fatty acid (6) having a carbon number of from 10 to 22 with a metal hydride so as to form an unsaturated fatty alcohol (7); (Step 202) epoxidizing the unsaturated fatty alcohol 7 to form an epoxy-alcohol species (8) comprising an epoxide ring; (Step 203) opening the ring of the epoxy-alcohol species 8 to form a triol (9); and (Step 204) esterifying the triol 9 with an esterifying species (10) to form a triester species (11), wherein the esterifying species 10 is selected from the group consisting of carboxylic acids, acyl halides, acyl anhydrides, and combinations thereof, and wherein the esterifying species have a carbon number of from 2 to 18. In some such embodiments, said method can yield a mixture of triester species within the resulting lubricant composition by utilizing, in one or both of Steps 201 and 204, reagents that comprise a range of carbon number.

Generally, lubricant compositions made by such methods and comprising such triester species have a viscosity of 3 mm$^2$/s (centistokes) or more at a temperature of 100° C. and they typically have a pour point of less than −20° C., and selection of reagents and/or mixture components is typically made with this objective.

In some embodiments, where a quantity of such triester species is formed, the quantity of triester species can be substantially homogeneous, or it can be a mixture of two or more different such triester species. In any such embodiments, such triester compositions can be further mixed with one or more base oils of the type Group I-III. Additionally or alternatively, in some embodiments, such methods further comprise a step of blending the triester composition(s) with one or more diester and/or monoester species. In some such additional and/or alternative embodiments, some or all of the one or more diester species are as described in commonly-assigned U.S. patent Ser. No. 11/673,879; filed Feb. 12, 2007 and published as United States Patent Publication No. 20080194444.

In some embodiments, such methods produce compositions (vide supra) comprising at least one triester species selected from among the following: octadecane-1,9,10-triyl trihexanoate (1); octadecane-1,9,10-triyl triheptanoate; octadecane-1,9,10-triyl trioctanoate (2); octadecane-1,9,10-triyl trinonoate; octadecane-1,9,10-triyl tris(decanoate) (3); octadecane-1,9,10-triyl tridodecanoate (4); octadecane-1,9,10-triyl triundecanoate; octadecane-1,9,10-triyl tridodecanoate; octadecane-1,9,10-triyl tridecanoate; and octadecane-1,9,10-triyl tritetradecanoate (5); and mixtures thereof.

In some such above-described method embodiments, the mono-unsaturated fatty acid can be a bio-derived fatty acid formed by hydrolysis of one or more triglyceride-containing vegetable oils such as, but not limited to, palm oil, sunflower oil, rapeseed oil, olive oil, linseed oil, and the like. Other sources of triglycerides, for which hydrolysis can yield unsaturated fatty acids, include, but are not limited to, algae, animal tallow, and zooplankton. See, e.g., Bajpai et al., "Biodiesel: Source, Production, Composition, Properties and Its Benefits," J. Oleo Sci., vol. 55(10), pp. 487-502, 2006 (general review); Sargent et al., "Biosynthesis of Lipids in Zooplankton from Saanich Inlet, British Columbia, Canada," Marine Biology, vol. 31, pp. 15-23, 1975 (zooplankton as a source of lipids).

In some embodiments, wherein the above-mentioned hydrolyzed triglyceride sources contain mixtures of saturated fatty acids, mono-unsaturated fatty acids, and poly-unsaturated fatty acids, one or more techniques may be employed to isolate, concentrate, or otherwise separate the mono-unsaturated fatty acids from the other fatty acids in the mixture. See, e.g., commonly-assigned United States Patent Application by Miller entitled, "Isolation and Subsequent Utilization of Saturated Fatty Acids and α-Olefins in the Production of Ester-Based Biolubricants," Ser. No. 12/122,894, filed May 19, 2008.

In some embodiments, partial hydrogenation of polyunsaturated fatty acids can yield mono-unsaturated fatty acids for use in methods of the present invention. Post hydrogenation, such mono-unsaturated fatty acids may be subjected to one or more of the above-mentioned separation/isolation techniques. See, e.g., Falk et al., "The Effect of Fatty Acid Composition on Biodiesel Oxidative Stability," Eur. Journal of Lipid Sci. & Technol., vol. 106(12), pp. 837-843, 2004.

Regarding the step of metal-hydride reduction, in some embodiments, lithium aluminum hydride (LiAlH$_4$) is used as the reducing agent. In some or other embodiments, particularly for industrial-scale processes, catalytic hydrogenation is employed using, for example, copper- or zinc-based catalysts. See, e.g., U.S. Pat. No. 4,880,937; Scrimgeour, "Chemistry of Fatty Acids," in *Bailey's Industrial Oil and Fat Products, 6$^{th}$ Edition*, Vol. 1, pp. 1-43, F. Shahidi (Ed.), J. Wiley & Sons, New York, 2005.

Regarding the step of epoxidizing (i.e., the epoxidation step), in some embodiments, the above-described unsaturated fatty alcohol can be reacted with a peroxide (e.g., H$_2$O$_2$) or a peroxy acid (e.g., peroxyacetic acid) to generate an epoxy-alcohol species. See, e.g., Swern et al., "Epoxidation of Oleic Acid, Methyl Oleate and Oleyl Alcohol with Perbenzoic Acid," J. Am. Chem. Soc., vol. 66(11), pp. 1925-1927, 1944.

Regarding the step of epoxide ring opening to the corresponding triol, this step can involve an acid-catalyzed hydrolysis. Exemplary acid catalysts include, but are not limited to, mineral-based Brönsted acids (e.g., HCl, H$_2$SO$_4$, H$_3$PO$_4$, perhalogenates, etc.), Lewis acids (e.g., TiCl$_4$ and AlCl$_3$), solid acids such as acidic aluminas and silicas or their mixtures, and the like. See, e.g., Parker et al., "Mechanisms of Epoxide Reactions," Chem. Rev., vol. 59(4), pp. 737-799, 1959; and Paterson et al., "meso Epoxides in Asymmetric Synthesis: Enantioselective Opening by Nucleophiles in the Presence of Chiral Lewis Acids," Angew. Chem. Int. Ed., vol. 31(9), pp. 1179-1180, 1992. The epoxide ring opening to the diol can also be accomplished by base-catalyzed hydrolysis using, for example, aqueous solutions of KOH or NaOH.

Regarding the step of esterifying the triol to form a triester, an acid can be used to catalyze the reaction between the —OH groups of the diol and the carboxylic acid(s). Suitable acids include, but are not limited to, sulfuric acid (Munch-Peterson, Org Synth., Coll. Vol. 5, p. 762, 1973), sulfonic acid (Allen and Sprangler, Org Synth., Coll. Vol. 3, p. 203, 1955), hydrochloric acid (Eliel et al., Org Synth., Coll. Vol. 4, p. 169, 1963), and phosphoric acid (among others). In some embodiments, the carboxylic acid used in this step is first converted to an acyl chloride (or another acyl halide) via, e.g., thionyl chloride or PCl$_3$. Alternatively, an acyl chloride (or other acyl halide) could be employed directly. Where an acyl chloride is used, an acid catalyst is not needed and a base such as pyridine, 4-dimethylaminopyridine (DMAP) or triethylamine (TEA) is typically added to react with an HCl produced. When pyridine or DMAP is used, it is believed that these amines also act as a catalyst by forming a more reactive acylating intermediate. Accordingly, such esterification steps can also be base-catalyzed. See, e.g., Fersht et al., "Acetylpyridinium ion intermediate in pyridine-catalyzed hydrolysis and acyl transfer reactions of acetic anhydride. Observation, kinetics, structure-reactivity correlations, and effects of concentrated salt solutions," J. Am. Chem. Soc., vol. 92(18), pp. 5432-5442, 1970; and Höfle et al., "4-Dialkylaminopyradines as Highly Active Acylation Catalysts," Angew. Chem. Int. Ed. Engl., vol. 17, pp. 569-583, 1978. Additionally or alternatively, the carboxylic acid could be converted into an acyl anhydride and/or such species could be employed directly.

Regardless of the source of the mono-unsaturated fatty acid (vide supra), in some embodiments, the carboxylic acids (or their acyl derivatives) used in the above-described methods are derived from biomass. In some such embodiments, this involves the extraction of some oil (e.g., triglyceride) component from the biomass and hydrolysis of the triglycerides of which the oil component is comprised so as to form free carboxylic acids. Other sources of such carboxylic acids include, but are not limited to, those derived (directly or indirectly) from FT synthesis.

5. Variations

Variations on the above-described methods include, but are not limited to, generating (and utilizing) compositional ranges of triesters by blending and/or by compositional variation in the reagents used during the synthesis of the triester species described herein. Compositions produced by such method variations will, naturally, be variations themselves. Generally, all such variations fall within the scope of the compositions and methods described herein.

In some variational embodiments, molecular averaging can be employed to generate greater molecular homogeneity in the resulting compositions (at least in terms of the triester species contained therein). Such molecular averaging techniques involve olefin metathesis and are generally described in the following U.S. Pat. Nos. 6,566,568; 6,369,286; and 6,562,230.

In some or other variational embodiments, the olefinic portion of the mono-unsaturated fatty alcohol can be efficiently transformed to the corresponding triol by highly selective reagents such as osmium tetra-oxide (M. Schroder, "Osmium tetraoxide cis hydroxylation of unsaturated substrates," Chem. Rev., vol. 80(2), pp. 187-213, 1980) and potassium permanganate (Sheldon and Kochi, in *Metal-Catalyzed Oxidation of Organic Compounds*, pp. 162-171 and 294-296, Academic Press, New York, 1981).

In some or still other variational embodiments, the sequence of reaction steps in producing the triol species can be modified as described, e.g., in Example 3 (vide infra).

6. EXAMPLES

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Figure 3:
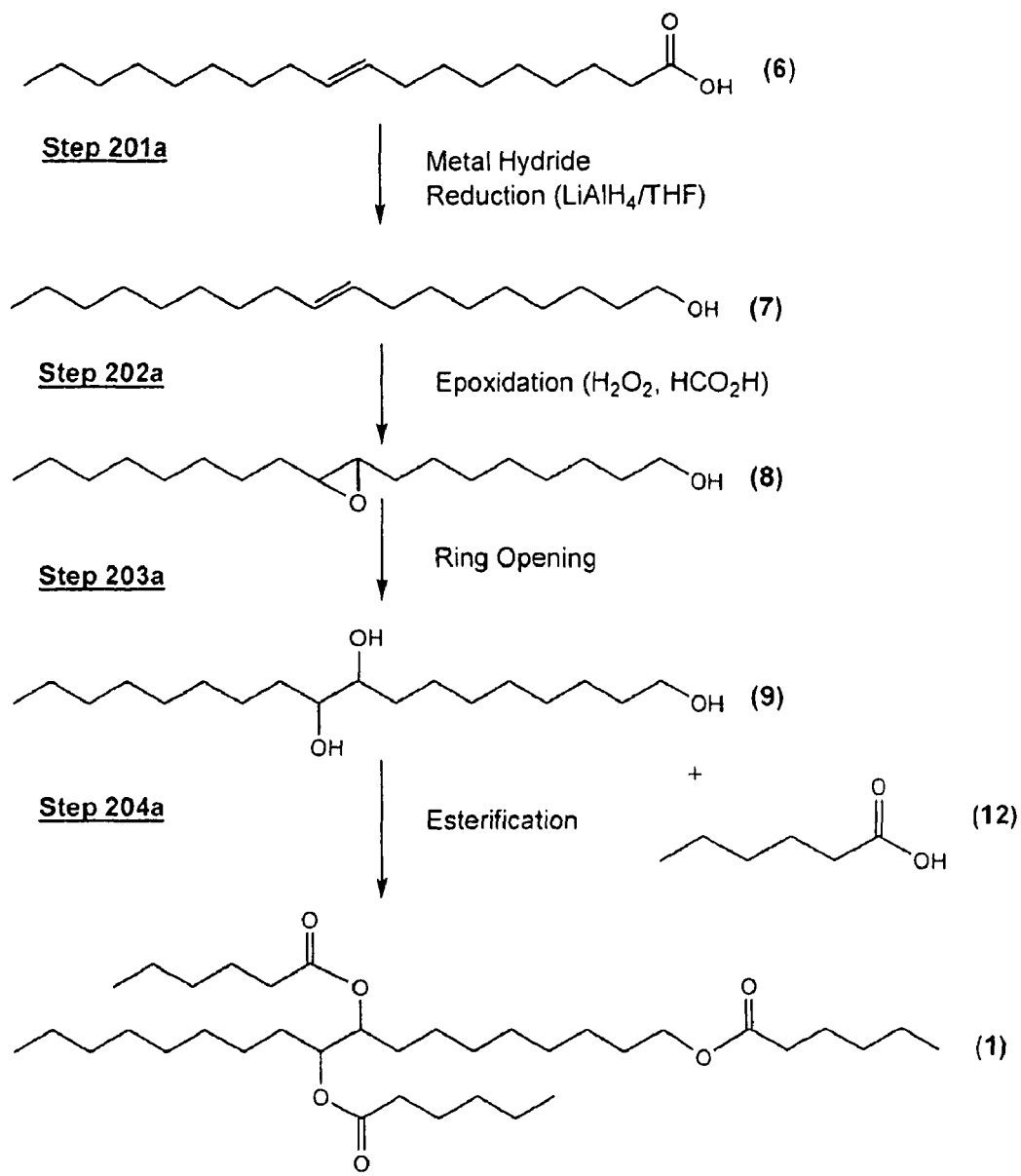
FIG. 3 (Scheme 2) is a chemical flow diagram illustrating an exemplary method of making triester composition 1, in accordance with some embodiments of the present invention.

As an exemplary synthetic procedure, the synthesis of triester 1 (Scheme 2, FIG. 3) is described in Examples 1-4. This procedure is representative for making triesters from mono-unsaturated fatty acids, in accordance with some embodiments of the present invention.

Example 1

This Example serves to illustrate synthesis of oleoyl alcohol 7 (an exemplary monounsaturated fatty acid), via a reduction of oleic acid (Step 201a), en route to synthesis of exemplary triester 1 and in accordance with some embodiments of the present invention. Oleoyl alcohol 7 was prepared according to the following procedure.

To an ice-cold (ice bath) suspension of 43 grams (1.13 mol) of lithium aluminum hydride ($LiAlH_4$) in tetrahydrofuran (THF) in a 3-neck 3-liter reaction flask fitted with an overhead stirrer and a reflux condenser, 150 grams (0.53 mol) of oleic acid 6 was added drop-wise over a period of 45 minutes via an addition funnel. The resulting reaction mixture was allowed to warm gradually to room temperature, after which the ice bath was replaced with a heating mantle and the reaction mixture was refluxed for 4 hours. After reflux, the reaction mixture was allowed to cool to room temperature and stirred overnight. The reaction progress was monitored by infrared (IR) and nuclear magnetic resonance (NMR) spectroscopies for the disappearance of the acid carbonyl group. The reaction was worked up by dilution with 500 mL diethyl ether followed by slow addition (drop-wise) of 350 mL of 15 wt % NaOH aqueous solution at 0° C. with vigorous stirring followed by the addition of 50 mL of water. The resulting 2-layer solution, a white solid precipitate and clear organic layer, was filtered to remove the solids (i.e., the unwanted inorganic salts). The organic layer was dried over anhydrous $MgSO_4$, filtered and concentrated on a rotary evaporator to give the mono-unsaturated fatty alcohol as a colorless oil. The reaction afforded 133 grams (93%) of the desired oleoyl alcohol 7. The product was authenticated with NMR, IR, and gas-chromatography/mass spectrometric (GC/MS) analyses.

Example 2

This Example serves to illustrate the synthesis of the octadecane-1,9,10-triol 9 (an exemplary triol) (Steps 202a and 203a), en route to the synthesis of triester species 1 and in accordance with some embodiments of the present invention. The triol 9 was prepared according to the following procedure.

To an ice-cold solution of hydrogen peroxide (110 grams of 30 wt % $H_2O_2$) and formic acid (250 grams of 88 wt % $HCO_2H$) in a 1 L, 3-neck reaction flask, 130 grams of oleoyl alcohol 7 (prepared as described in Example 1 above) were added drop-wise over 45 minutes. Once the addition was complete, the reaction was allowed to slowly warm to room temperature and then heated to 40° C. for 3 hours. The reaction was subsequently allowed to stir over night at room temperature. The reaction was stripped on a rotary evaporator to remove excess formic acid. The residual mixture of the triol 9 and its formates was treated with an ice cold solution of sodium hydroxide (45 grams NaOH in 100 grams water) in small portions. The addition was done slowly and carefully and the temperature was kept around 40° C. Once the addition of NaOH was completed, the mixture was diluted with 500 mL ethyl acetate and heated to 45° C. The aqueous layer was separated from the organic layer using a separatory funnel. The aqueous layer was thoroughly extracted with hot ethyl acetate. The acetate extracts were combined with the original organic layer and concentrated on a rotary evaporator to give the triol 9 as a white solid material in 91% yield (133 grams). NMR and GCMS analysis showed the product to be >95% pure. No further purification was done. The product was taken directly to the next step (Example 4).

Example 3

This Example serves to illustrate how the sequence of steps leading to the triol can be altered, in accordance with some embodiments of the present invention.

Using a procedure similar to that described in Example 2 (in terms of quantities, reagents), oleic acid 6 was derivatized to the corresponding 9,10-dihydrolyloleic acid which was then reduced with lithium aluminum hydroxide to the corresponding triol derivative 9.

Example 4

This Example serves to illustrate the synthesis of triester 1 from the triol, e.g., 9. The synthesis of octadecane-1,9,10- triyl trihexanoate 1 described below is representative of the synthesis of these types of triesters.

In a 250 mL 3-neck reaction flask fitted with an overhead stirrer, a nitrogen bubbler, and a Dean-Stark trap, 50 grams (0.16 mol) of the triol 9, prepared as described in Example 2 above, were mixed with 87 grams (0.75 mol) of hexanoic acid 12 and 0.9 grams of 85 wt % $H_3PO_4$ at room temperature. The resultant mixture was stirred and heated to 160° C. with nitrogen bubbling through it. After 12 hours, the reaction was complete, and was cooled to room temperature. The mixture was washed thoroughly with water, dried over $MgSO_4$ and filtered. The mixture was distilled under a vacuum of 100 mm Hg to remove excess hexanoic acid. The desired triester product 1 was obtained in 73% yield (72 grams). Triester species 1 was determined to have lubricant properties as listed in Table 1 (FIG. 4).

7. Summary

In summary, the present invention provides for triester-based lubricant compositions. The present invention also provides for methods (processes) of making these and other similar lubricant compositions. In some embodiments, the methods for making such triester-based lubricants utilize a biomass precursor comprising mono-unsaturated fatty acids, wherein such mono-unsaturated fatty acids are reduced to mono-unsaturated fatty alcohols en route to the synthesis of triester species for use as/in the triester-based lubricant compositions. Subsequent steps in such synthesis may employ carboxylic acids and/or acyl halides/anhydrides derived from biomass and/or Fischer-Tropsch synthesis.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method comprising the steps of:
    a) reducing a mono-unsaturated fatty acid having a carbon number of from 10 to 22 with a metal hydride so as to form an unsaturated fatty alcohol;
    b) epoxidizing the unsaturated fatty alcohol to form an epoxy-alcohol species comprising an epoxide ring;
    c) opening the ring of the epoxy-alcohol species to form a triol; and
    d) esterifying the triol with an esterifying species to form a triester species, wherein the esterifying species is selected from the group consisting of carboxylic acids, acyl halides, acyl anhydrides, and combinations thereof, and wherein the esterifying species have a carbon number of from 2 to 18.

2. The method of claim 1, wherein the step of esterifying the triol with an esterifying species involves a catalyst selected from the group consisting of an acid catalyst and a base catalyst.

3. The method of claim 1, wherein the step of esterifying the triol with an esterifying species involves conversion of a fatty acid to an acyl halide species selected from the group consisting of acyl chlorides, acyl bromides, acyl iodides, and combinations thereof.

4. The method of claim 1, wherein the step of esterifying the triol with an esterifying species involves conversion of a fatty acid to an acyl anhydride species.

5. The method of claim 1, further comprising a step of blending the triester species with one or more other ester species selected from the group consisting of triesters, diesters, monoesters, and combinations thereof.

6. The method of claim 1, wherein the triester species is entirely bio-derived.

7. The method of claim 1, further comprising a step of blending the triester species with a base oil selected from the group consisting of Group I oils, Group II oils, Group III oils, and combinations thereof.

8. The method of claim 1, wherein said method yields a mixture of triester species by utilizing, in one or both of steps (a) and (d), reagents that comprise a range of carbon number.

* * * * *